US005677139A

United States Patent [19]
Johnson et al.

[11] Patent Number: 5,677,139
[45] Date of Patent: Oct. 14, 1997

[54] IN VITRO DIFFERENTIATION OF CD34+ PROGENITOR CELLS INTO T LYMPHOCYTES

[75] Inventors: R. Paul Johnson, Lexington; Michael Rosenzweig, Boston; David T. Scadden, Weston, all of Mass.

[73] Assignee: President and Fellows of Harvard College, Cambridge, Mass.

[21] Appl. No.: 426,782

[22] Filed: Apr. 21, 1995

[51] Int. Cl.$^6$ ............................................ C12Q 1/02
[52] U.S. Cl. ................... 435/29; 435/172.3; 435/363; 435/372.3; 435/373
[58] Field of Search ........................ 435/240.2, 240.1, 435/7.21, 7.24, 172.3, 320.1, 29, 4, 2, 363, 372.3, 373

[56] References Cited

PUBLICATIONS

Rosenzweig et al. 1994 abstract for New England Immunology Conference, Oct. 22, 1994.
Tjønnfjord et al. 1993 J. Exp Med 177:1531–1539.
Tatsumi et al. 1990 Proceedings of the Nat'l Acad. of Sciences USA 87:2750–2754.
Plum et al. 1994 Blood 5:1587–1593.
Ilstad et al. 1991. J. Exp. Med. 467–478.
Bárcena et al. 1994 J. Exp. Med 180:123–132.
de la Hera et al. 1989 Int. Immunol. 1:471–478.
Kohn, D.B. 1995 Current Opinion in Pediatrics 7:56–63.
Meco et al. 1994 J. Immunol. 153: 73–83.
Akkina et al., Modeling human lymphoid precursor cell gene therapy in the SCID–hu mouse, Blood 84: 1393–1398, 1994.
Aldrovandi et al., The SCID–hu mouse as a model for HIV–1 Infection, Nature 363: 732–736, 1993.
Bonyhadi et al., HIV induces thymus depletion in vivo, Nature 363: 728–732, 1993.
Chen et al., Engraftment of human hematopoietic precursor cells with secondary transfer potential in SCID–hu mice, Blood 84: 2497–2505, 1994.
Dorshkind, Transcriptional control points during lymphopoiesis, Cell 79:751–753, 1994.
Egeland et al., CD34: The gateway to the study of lympho-hematopoietic progenitor and leukemic cells, The Immunol. 2: 65–70, 1994.
Galy et al., Precursors of CD3+ CD4+ CD8+ cells in the human thymus are defined by expression of CD34, Delineation of early events in human thymic development, J. Exp. Med. 178: 391–401, 1993.
Lanier et al., The developmental relationship between NK cells and T cells, Immunol. Today 13: 392–395, 1992.
Oettinger et al., RAG–1 and RAG–2, adjacent genes that synergistically activate V(D)J recomination, Science 248: 1517–1523, 1990.
Peault et al., Lymphoid reconstitution of the human fetal thymus in SCID mice with CD34+ precursor cells, J. Exp. Med. 174: 1283–1286, 1991.

Phillips et al., Ontogeny of human natural killer (NK) cells: Fetal NK cells mediate cytolytic function and express cytoplasmic CD3 proteins, J. Exp. Med. 175: 1055–1066, 1992.
Sanchez et al., Human natural killer cell committed thymocytes and their relation to the T cell lineage, J. Exp. Med. 178: 1857–1866, 1993.
Singer et al., In vitro growth and phenotypic characterization of mesodermal–derived and epithelial components of normal and abnormal human thymus, Human Immunol. 13: 161–176, 1985.
Terstappen et al., Sequential generations of hematopoietic colonies derived from single nonlineage–committed CD34+CD38–progenitor cells, Blood 77: 1218–1227, 1991.
Tjonnfjord et al., T lymphocyte differentiation in vitro from adult human prethymic CD34+ bone marrow cells, J. Exp. Med. 177: 1531–1539, 1993.
van Ewijk, T–cell differentiation is influenced by thymic microenvironments, Annu. Rev. Immunol. 9: 591–615, 1991.
Barcena et al., Lymphoid and myeloid differentiation of fetal liver CD34+lineage cells in human thymic organ culture, J. Exp. Med. 180:?? 123–132, 1991??.
Plum et al., Human CD34+ fetal liver stem cells differentiate to T cells in a mouse thymic microenvironment, Blood 5: 1587–1593, 1994.
Yeoman et al., Human bone marrow and umbilical cord blood cells generate CD4+ and CD8+ single–positive T cells in murine fetal thymus organ culture, Proc. Nat. Acad. Sci. USA 90: 10778–10782, 1993.
Rosenzweig et al., In vitro differentiation of CD34+ bone marrow derived cells into mature T lymphocytes and natural killer cells, Abstract presented at: New England Immunology Conference, Oct. 22, 1994.
Sutherland et al., Long–term culture of human myeloid cells, In: Culture of Hematopoietic Cells, Eds Freshney et al., pp. 139–162, 1994.
Kawai et al., Characterization of a monoclonal antibody (6G12) recognizing the cynomolgus monkey CD3 antigen, Transplant Proc. 26: 1845–1846, 1994.
Chen et al., Cell receptor repertoire in Simian Immunodeficiency Virus–infected Rhesus monkeys, J. Immunol. 151: 2177–2187, 1993.

(List continued on next page.)

Primary Examiner—James Ketter
Assistant Examiner—Irem Yucel
Attorney, Agent, or Firm—Wolf, Greenfield & Sacks, P.C.

[57] ABSTRACT

The invention involves a method for the in vitro T cell production. A monolayer of non-human primate thymic stromal cells are cocultured in vitro with primate hematopoietic T cell progenitor cells. This results in the differentiation and growth of mature T cells. The T cells may be isolated at any sequential stage of differentiation and further expanded by coculture with a mitogenic agent. The T cells also may be genetically altered at any stage of the process. The effect of agents on the growth and differentiation of T cells may be measured by comparing a coculture containing the agent with a control coculture and comparing the differentiation or growth of the T cells progenitor cells in the test culture with the control culture. Kits and novel populations of T cells are provided.

22 Claims, No Drawings

PUBLICATIONS

Scheid et al., Differentiation of T cells induced by preparations from thymus and nonthymic agents, J. Exp. Med. 138: 1027–1032, 1973.

Meco et al., Modulation of fibronectin and thymic stromal cell–dependent thymocyte maturation by retinoic acid, J. Immunol. 153: 73–83, 1994.

Spooncer et al., Self–renewal and differentiation of interleukin–3–dependent multipotent stem cells are modulated by stromal cells and serum factors, Differentiation 31: 111–118, 1986.

Quesenberry et al., Stromal cell regulation of lymphoid and myeloid differentiation, Blood Cells 13: 137–146, 1987.

Ildstad et al., Cross–species bone marrow transplantation: evidence for tolerance induction, stem cell engraftment, and maturation of T lymphocytes in a xenogeneic stromal environment (rat–mouse), J. Exp. Med. 174: 467–478, 1991.

Tatsumi et al., Differentiation of thymocytes from CD3–CD4–CD8– through CD3–CD4–CD8+ into more mature stages induced by a thymic stromal cell clone, Proc. Nat. Acad. Sci. USA 87: 2750–2754, 1990.

Fujiwara et al., Proliferation and differentiation of immature thymocytes induced by a thymic stromal cell clone, Thymus 16: 159–172, 1990.

Waanders et al., Modulation of T–cell differentiation in murine fetal thymus organ cultures, Thymus 13: 73–82, 1989.

de la Hera et al., Thymic stroma is required for the development of human T cell lineages in vitro, Int. Immunol. 1: 471–478, 1989.

Eren et al., Syngeneic preference manifested by thymic stroma during development of thymocytes from bone marrow cells, Eur. J. Immunol. 19: 2087–2092, 1989.

Splitter et al., The differentiation of bone marrow cells to functional T lymphocytes following implantation of thymus grafts and thymic stroma in nude and ATxBM mice. Cell. Immunol. 34: 93–103, 1977.

Anderson et al., Characteristics of an in vitro system of thymocyte positive selection. J. Immunol. 153:1915–1920, 1994.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Macaca mulatta (x i) SEQUENCE DESCRIPTION: SEQ ID NO:1:

GTCCCGGGCG CTGCA                                                                                    15

(2) INFORMATION FOR SEQ ID NO:2:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Macaca mulatta (xi) SEQUENCE DESCRIPTION: SEQ ID NO:2:

CCTCCCACAC GCTTGCAGT                                                                                19

(2) INFORMATION FOR SEQ ID NO:3:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Macaca mulatta (xi) SEQUENCE DESCRIPTION: SEQ ID NO:3:

CGTTGGGTCG GTGTCAGCCA CTCTCACCTC CC                                                                 32

IN VITRO DIFFERENTIATION OF CD34+ PROGENITOR CELLS INTO T LYMPHOCYTES

GOVERNMENT SUPPORT

This invention was supported by NIH Grant NOS.RROO168,AI36550 and HL44851, and the government has certain rights to the invention.

FIELD OF THE INVENTION

The invention pertains to the growth and differentiation of T cells, and the genetic alteration of such T cells.

BACKGROUND OF THE INVENTION

Lymphoid differentiation of hematopoietic progenitor cells is dependent on interactions of these cells with thymic tissue. The prerequisite for these interactions has hindered the development of an in vitro system of lymphocyte differentiation. Lymphocytes originate from pluripotent stem cells that originate in the fetal liver and bone marrow. T lymphocyte differentiation normally occurs via a series of discrete developmental stages involving an initial primitive progenitor cell without lymphocyte specific cell surface markers ($CD34^+CD3^-CD4^-CD8^-$), followed by acquisition of lymphocyte specific markers and loss of CD34 ($CD34^- CD3^+CD4^+CD8^+$), followed by differentiation into mature $CD3^+$ T cells expressing either CD4 or CD8 ($CD3^+CD4^+ CD8^-$ or $CD3^+CD4^-CD8^+$). Hematopoietic stem cells that are self renewing and pluripotent constitute approximately 1% of low density nucleated bone marrow cells. These cells express a high level of CD34 antigen on their surface, and as these pluripotent cells develop and commit to either the lymphoid, monomyeloid or erythroid cell series, the level of CD34 decreases.

Because T lymphocyte differentiation requires the interaction of precursor cells with thymic tissue, efforts to study this process in the laboratory have been quite limited. The study of human lymphopoiesis has been largely confined to the SCID-hu mouse in vivo model, thymic explant studies and human thymic monolayers. However, these existing techniques all share some significant drawbacks, among them a relatively low efficiency of T cell differentiation, the limited number of cells available for functional studies, and the difficulty in obtaining a readily available and consistent source of thymic tissue.

Recent progress using gene therapy to treat diseases involving T lymphocytes, including AIDS, has fostered increased interest in the development of laboratory techniques that allow in vitro evaluations of potential genetic therapies for these disorders. Existing techniques have not permitted detailed evaluation of the properties of candidate therapeutic genes in T lymphocytes derived from genetically modified progenitor cells. Techniques such as the SCID-hu mouse yield only a small number of transduced T cells in mouse tissue. Extremely sensitive techniques such as polymerase chain reaction are necessary to detect foreign genes in these cells and sufficient numbers are not available to allow assessment of potential toxicity or to examine whether the therapeutic gene has had the desired effect, i.e. production of an enzyme or protection of the T cell against HIV infection.

We describe a system using non-human primate thymic derived cells that provides the appropriate conditions for in vitro T cell differentiation of human and non-human primate hematopoietic progenitor cells. T lymphocytes derived from these cultures respond normally to a variety of stimuli and express the diversity expected of mature T cells. This system provides significant advantages over existing techniques in that it: 1) replicates the complex process of T lymphocyte differentiation more closely than existing techniques, as evidenced by the normal progression of thymocyte stages observed at successive time points in vitro and the diverse representation of T cell receptors in T cells derived from these cultures; 2) provides a relatively large number of T cells necessary for laboratory analysis and therapeutic use including in vitro testing of potential gene therapy strategies and reinfusion into subjects in vivo; and 3) provides the capability to support in vitro T cell differentiation using a reagent that is available in relatively large amounts, thereby minimizing inter assay variation and enhancing quality control. Existing thymic culture techniques, particularly those involving SCID-hu mice, suffer from significant experiment to experiment variation. In contrast, since between $10^9$ and $10^{10}$ cells (sufficient for up to 10,000 assays) may be obtained and cryopreserved from a thymus harvested from a single animal, a large quantity of cells may be stored and used for multiple experiments.

SUMMARY OF THE INVENTION

According to one aspect of the invention, a method for in vitro T cell production is provided. The method involves coculturing in vitro a monolayer of non-human primate thymic stromal cells with primate hematopoietic T cell progenitor cells.

Preferably the thymic stromal cells are derived from a member of the species *Macaca mulatta* or *Macaca fascicularis*, most preferably *Macaca mulatta*. The preferred progenitor cells are derived from a member of the species *Homo sapiens*.

The hematopoietic T cell progenitor cells or descendants thereof can be isolated from the monolayer of thymic stromal cells at any time during the sequential stages of differentiation of such cells. In particular, the progenitor cells or descendants thereof may be isolated from the monolayer prior to the differentiation of a substantial portion of such cells into either $CD3^+4^+8^-$ or $CD3^+4^-8^+$ cells.

The hematopoietic T cell progenitor cells or descendants thereof also may be cultured with a mitogenic agent to stimulate expansion of the cells or descendants thereof. Such expansion can occur, optionally, isolated from the stromal monolayer and in a state of arrested differentiation, that is, growth without further differentiation. Optionally, isolated and expanded cells can be reintroduced into culture with a monolayer of thymic stromal cells to promote further differentiation. According to one preferred embodiment, the predominant cell type isolated for expansion is $CD3^+4^+8^+$. It is likewise contemplated that fully differentiated cells ($CD3^+ 4^+8^-$ and $CD3^+4^-8^+$ cells) can be cultured with a mitogenic agent to stimulate the expansion of such cells. The preferred mitogenic agent is non-mitotic feeder cells such as irradiated peripheral blood mononuclear cells.

According to another aspect of the invention, the hematopoietic T cell progenitor cells are genetically altered T cell progenitor cells. Such genetic alteration can occur prior to coculturing the hematopoietic T cell progenitor cells with the thymic stromal cells or at any stage during the coculture of the hematopoietic T cell progenitor cells with the thymic stromal cells. The progenitor cells or descendants thereof then can be isolated.

According to another aspect of the invention, a method for testing the effect of an agent on cells is provided. A monolayer of non-human primate thymic stromal cells is cocultured in vitro with primate hematopoietic T cell progenitor cells in the presence of the agent. The differentiation or growth of the T cell progenitor cells, or descendants thereof, exposed to the agent then is compared to the differentiation or growth of control T cell progenitor cells or descendants thereof as a determination of the effect of the agent. The conditions of culture, including the cell types, expansion conditions, genetic alteration and the like, can be varied as described above.

According to another aspect of the invention, a kit is provided. The kit includes a container containing a cryopreserved non-human primate thymic stromal cell suspension and instructions for coculture of a monolayer of the thymic stromal cells with primate (including humans) hematopoietic T cell progenitor cells. The preferred cells are as described above. Such kits may be shipped to remote locations for thawing, forming the stromal monolayer and coculturing to promote in vitro T cell growth and differentiation.

According to still another aspect of the invention, an article of manufacture is provided. The article of manufacture is a container containing a representative population of T cells derived by any of the foregoing methods. Preferably the representative population of T cells is derived by the method of claim 1 and most preferably the representative population of T cells is derived by culturing cells isolated from the coculturing conditions of claim 1 and further culturing the isolated cells with a mitogen to stimulate the expansion of such isolated cells.

It thus is an object of the invention to provide methods permitting the in vitro growth and differentiation of T cells.

Another object of the invention is to provide a test system for evaluating the effects of agents on T cell growth and differentiation.

Another object of the invention is to provide methods for yielding in vitro high numbers of T cells.

Another object of the invention is to provide methods of providing in vitro high numbers of T cells arrested at various stages of development.

Another object of the invention is to provide methods for genetically altering T cells in vitro.

Another object of the invention is to provide methods for expanding T cells in vitro for reintroduction of such cells in vivo.

Another object of the invention is to provide in vitro T cell differentiation that results in a substantially full repertoire of T cell types and results in T cells that respond similarly to those isolated from a subject.

These and other objects of the invention will be described in greater detail below.

DETAILED DESCRIPTION OF THE INVENTION

Thymic stromal cells are derived from the disaggregation of a piece of thymus tissue. Such cells according to the invention are capable of supporting in vitro T cell growth and differentiation. Thymic stromal cells may include, but are not limited to, all cell types present in the thymus which are not lymphocytes or lymphocyte precursors or progenitors, e.g., epithelial, mesothelial cells, dendritic cells and macrophages.

Thymic stromal cells provide the supporting microenvironment in the intact thymus for the differentiation of T cell progenitor cells to mature T cells. The microenvironment includes soluble and cell surface factors expressed by the various cell types which comprise the thymic stroma.

Thymic stroma cells may be obtained from the thymus of a non-human primate at any time after the organ has developed to a stage at which it can support the differentiation of T cells. In primates, this stage of thymic development is achieved during the second trimester. At this stage of development the thymus can produce peptide hormones such as thymulin, $\alpha_1$ and $\beta_4$-thymosin, and thymopoietin, as well as other factors required to provide the proper microenvironment for T cell differentiation. It is preferred that the stromal cells are derived from a non-human primate thymus during the third trimester of gestation or from a thymus of a non-human primate neonate. During the mid to late third trimester, the thymus stromal microenvironment is fully capable of inducing the differentiation of T cell progenitor cells to mature T cells.

The non-human primate stromal cells can be derived from any non-human primate. Examples include: *Aotus trivirgatus*—owl monkey; *Ateles geoffroy*—spider monkey; *Cebus albifrons*—white and brown capuchin monkey; *Callithrix jacchus*—common marmoset monkey; *Cercopithecus aethiops*—African green monkey; *Galago crassicaudatus*—Bushbaby monkey; *Macaca arctoides*—stump-tailed macaque monkey; *Macaca cyclopis* formosan macaque monkey; *Macaca fascicularis*—Crab eater macaque (cynomolgus) monkey; *Macaca mulatta*—rhesus monkey; *Macaca nemistrina*—pig tail monkey; *Macaca sylvana*—barbary macaque; *Pan troglodytes*—chimpanzee; *Papio anubis*—baboon; *Papio cynocephalus*—yellow baboon; *Papio hamadryads*—chaema baboon; *Papio doguera*—Dog-faced baboon; *Saguinus fuscicollis*—tamarin monkey; *Saguinus oedipus*—Cotton top tamarin monkey; and *Saimiri sciureus*—squirrel monkey. A preferred non-human primate is *Macaca fascicularis* and the most preferred non-human primate *Macaca mulatta*.

The cells are then grown as a "monolayer". A monolayer of thymic stromal cells is recognized by one of ordinary skill in the art as an in vitro thymic stromal culture having a thickness of one or more cells. A monolayer of thymic stromal cells encompasses a non-confluent layer of stromal cells, a confluent layer of stromal cells having a thickness of a single cell, and a layer of stromal cells in which the cells are stacked on one another to a thickness of two or more cells. In all cases, such monolayers are formed of suspensions of cells disaggregated from their native tissue structure and organization, preferably into single cell suspensions, which then are plated into a vessel and permitted to attach to a surface. It is preferred that the cells be grown to confluency.

It should be noted that the stromal cells may be cryopreserved for later use or for storage and shipment to remote locations, such as for use in connection with the sale of kits. Cryopreservation of cells cultured in vitro is well established in the art. Subsequent to isolation of a cell sample, cells may be cryopreserved by first suspending the cells in a cryopreservation medium and then gradually freezing the cell suspension. Frozen cells are typically stored in liquid nitrogen or at an equivalent temperature in a medium containing serum and a cryopreservative such as dimethyl sulfoxide. Because of the large numbers of cells that can be obtained and preserved, the invention thus provides a reagent that is available in relatively large amounts, particularly for study of human T cells, thereby minimizing inter-assay variation and enhancing quality control.

Monolayers of the foregoing type are used to stimulate the growth and differentiation of primate hematopoietic T cell progenitor cells. This is accomplished by coculturing the monolayer together with the progenitor cells. Contact is contemplated for the most efficient stimulation.

Hematopoietic T cell progenitor cells are those cells capable of differentiating into mature T cells. They may be committed to the T cell lineage or uncommitted. T cell progenitor cells as used herein therefor include pluripotent cells which are capable of self-renewal and differentiation into all myeloid and lymphoid cell lineages, including T cells. T cell progenitor cells may be isolated from sources including bone marrow, umbilical cord blood or peripheral blood mobilized stem cells. Peripheral blood mobilized stem cells are obtained from the peripheral blood of subjects who have been treated with chemotherapeutic agents and/or cytokines to increase hematopoietic progenitor cells circulating in peripheral blood. The preferred hematopoietic T cell progenitor cells are those derived from humans.

Progenitor cells at various stages of differentiation may be used, although it is preferable to use progenitor cells in very early stages of differentiation. For example, $CD34^+CD38^-$ or $CD34^+CD38^+CD2^+$ progenitor cells have been used successfully. Hematopoietic stem cells that are self-renewing and pluripotent constitute approximately 0.01% of low density nucleated bone marrow cells. These cells express a high level of $CD34^+$ antigen on their surface and do not express CD38. These cells eventually develop and commit to lymphoid, monomyeloid or erythroid cells, including T cells. $CD34^+$ T cell progenitor cells are negative for the T cell markers CD3, CD4 and CD8. During differentiation to mature T cells, the progenitor cells pass through an intermediate stage during which the cells express CD3, CD4 and CD8 on the cell surface ($CD4^+CD8^+$: "double positive"). Immature T cells in this intermediate stage of differentiation lose expression of the CD34 cell surface marker. Mature T cells are $CD34^-CD3^+$, and are further characterized by the presence of only one of the cell surface markers CD4 and CD8. Mature T cells thus are either $CD4^+CD8^-$ or $CD4^-CD8^+$ ("single positive").

As will be seen in greater detail below in connection with the detailed examples, coculture of $CD34^+CD38^-$ T cell progenitor cells with a thymic stromal monolayer results in a expansion in the number of cells and in the differentiation of such cells into all stages including "single positive" cells. The repertoire of T cells produced more closely resembles the repertoire occurring in vivo than can be achieved by any known prior art method. The quantities of cells produced according to the present invention, particularly after expansion, also exceed by 40–100 times the known in vitro methods for generating T cells. The methods of the invention, nevertheless, are believed to result in populations of T cells which differ from those populations that can be isolated from any source in vivo in terms of the relative numbers of the various types of cells present. Therefore, novel populations of cells are provided according to the invention. Such novel populations are described in terms of "representative populations." A representative population of T cells derived according to the invention means a population of T cells which contains all of the subpopulation of T cells derived from the in vitro differentiation of T cell progenitor cells in coculture with thymic stromal cells and contains them in their relative amounts as results from such coculture. As such, a container containing such a representative population differs from any population previously isolated in terms of relative numbers of cell types.

It should be noted that the differentiation of T cells on the monolayer is sequential, and T cells at various stages of differentiation therefore can be isolated from the culture. For example, T cells that are $CD3^+4^+8^+$ predominate at certain times during the culturing period. In addition, cell sorting methodologies or sequential positive selection using magnetic beads may be used to further isolate such cells from other cell types. In particular it is possible to isolate T cell populations prior to their terminal differentiation into "single positive" cells. For example, at day 14 of coculture as described below in the examples, approximately 60% of the human cells are $CD3^+4^+8^+$. At day 28, the $CD3^+4^+8^+$ can represent less than 20% of the human cells. Conversely, at day 14 $CD4^+8^-$ cells can represent less than 25% of the human cells while at day 28 $CD4^-8^+$ cells can represent as many as 65% of the human cells. Likewise, $CD4-8^+$ cells can be as low as 2% on day 14 and as high as 15% on day 28.

It has been discovered that when such T cells are isolated from the stromal monolayer at a particular stage of differentiation, further expansion, for example, using mitogenic agents as discussed below, results in further growth of the cells but not further differentiation. Thus, the invention permits the isolation and expansion of high numbers of cells at a particular stage of differentiation. Such cells may be examined, for example, to test what mRNA they are producing and which receptors they are expressing. The relative effect of drugs on cells at different stages of differentiation may be tested. Likewise, such cells may be genetically altered at any particular stage of differentiation. It is further noted that such cells can be added back into culture with the stromal monolayer, with further differentiation reinitiated. Thus, for example, cells can be brought to a certain stage of development, isolated and genetically altered, and then further differentiated (optionally). Uses for such cells are further described below.

As mentioned above, the invention contemplates the further expansion of the hematopoietic T cells progenitor cells or descendants thereof. This is accomplished using a mitogenic agent and can be simply for increasing the number of cells available for use by those skilled in the art. Expansion can occur together in the culture with the stromal cells or isolated from the stromal cells. If together with the stromal cells, then growth and differentiation will occur. If isolated from the stromal cells, then growth may occur without further differentiation.

A mitogenic agent is an agent capable of supporting the expansion of a population of hematopoietic T cell progenitor cells or descendants thereof when incubated or cultured with such cells. Mitogenic agents are well known in the art and include agents that stimulate or support the growth of T lymphocytes. These agents include lectins, such as concanavalin A and phytohemagglutinin, and anti-CD3 antibody used alone or in combination with anti-CD28 antibody. These cells may also be cultured in the presence of agents such as cytokines, including the interleukins IL-2, IL-4, IL-6, IL-7, IL-9, IL-11, IL-12 and the flk ligand, and feeder cells.

Feeder cells encompass cells that are capable of supporting the expansion of hematopoietic T cell progenitor cells or descendants thereof. The support which the feeder cells provide may be characterized as both contact-dependent and non-contact-dependent. The feeder cells may secrete or express on the cell surface factors which support the expansion of the progenitor cells. One example of feeder cells is peripheral blood mononuclear cells. Other examples include splenocytes, lymph node cells and dendritic cells. Feeder cells also may be cells that would not ordinarily function as feeder cells, such as fibroblasts, which have been engineered to secrete or express on their cell surface the factors necessary for support of T cell progenitor cell expansion. Feeder cells may be allogeneic, syngeneic or xenogeneic with respect to the T cell progenitor cells.

Feeder cell are made non-mitotic by procedures standard in the tissue culture art. Examples of such methods are irradiation of feeder cells with a gamma-ray source or incubation of feeder cells with mitomycin C for a sufficient amount of time to render the cells mitotically inactive.

As mentioned above, the hematopoietic T cell progenitor cells, or descendants thereof, can be genetically altered. Genetic alteration of a hematopoietic T cell progenitor cell (or thymic stromal cell) includes all transient and stable changes of the cellular genetic material which are created by the exogenous addition of an agent. Examples of genetic alterations include any gene therapy procedure, such as introduction of a functional gene to replace a mutated or nonexpressed gene, introduction of a vector that encodes a dominant negative gene product, introduction of a vector engineered to express a ribozyme and introduction of a gene that encodes a therapeutic gene product. Natural genetic changes such as the spontaneous rearrangement of a T cell receptor gene without the introduction of any agents are not included in this concept.

Many agents capable of altering the genetic material of a cell are known to one of skill in the art. Such agents include vital vectors, episomal plasmid vectors, stably integrating plasmid vectors, and artificial chromosome vectors. Vital vectors include those derived from retroviruses, adenoviruses, adeno-associated viruses, herpesviruses, and pox viruses. Vital vectors may be delivered as virus particles or by another delivery mechanism as described below. Plasmid vectors include those plasmids that contain cDNAs, genomic DNAs and chimeric non-natural DNAs including synthetic nucleic acids. Vectors may be designed to integrate at a specific location in the genome by insertion or homologous recombination, may integrate randomly or may remain in the nucleus as a stable episomal nucleic acid. All of the above vectors may contain one or more genes or nucleic acid sequences.

The delivery of such genetic alteration agents may be accomplished by encapsulation in a vital particle or a synthetic particle such as a liposome. Many other delivery techniques are known in the art, including immunoconjugation, transfection and particle bombardment. Genetic alteration agents also include mutagens, antisense, ribozymes and the like.

Genetic alteration can be performed at any stage of differentiation of the hematopoietic T cell progenitor cells or descendants thereof. For example, the genetic alteration can be made directly on the cells as isolated from the primate (e.g., bone marrow, umbilical cord, etc.) or on a subpopulation thereof. Likewise, the genetic alteration can be carried out at any stage of the coculture, including during the coculture, or on any isolate of the coculture. In one preferred embodiment, retroviral vectors are used to genetically alter the cells during the coculture process in which the cells are dividing and differentiating. This promotes stable integration of the provirus into the genome of the dividing cells. Also as mentioned above, cells that have been isolated from a stromal monolayer and genetically altered can be reintroduced into culture with a stromal monolayer after the genetic alteration. The foregoing procedures have many utilities, including expanding the population of genetically altered cells for study or for therapeutic purposes as more fully described below.

According to another aspect of the invention, a method for testing the effect of an agent on cells is provided. The coculture of the stromal monolayer and primate hematopoietic T cell progenitor cells is carried out in the presence of the agent. The growth and differentiation of the T cell progenitor cells, or descendants thereof, exposed to the agent then is compared to the growth or differentiation of control T cell progenitor cells or descendants thereof as a determination of the effect of the agent. The cells utilized, the culture conditions, the length of time that the cells are cultured, the expansion conditions and the like can vary to the full extent as described above. What differs in this embodiment is the addition of an agent to the culture and a comparison of growth and/or differentiation to a control culture, preferably subject to otherwise identical conditions, but without the agent. The effect of the agent on the growth and differentiation of T cells can then be determined in this manner.

The agent can be anything known to be or suspected of being capable of affecting the growth and differentiation of the T cells. Examples include synthetic chemical agents, biochemical agents, cells, extracts, homogenates, and the like. The agent may act directly on T cell progenitors or decendants thereof or indirectly via action on the stromal layer. Specific examples include mitogens, cytokines, promoters of differentiation, antimetabolics, ribozymes, antisense, genes and pathogens such as viruses and bacteria. The foregoing is intended to be non-limiting; those skilled in the art will know numerous examples of agents useful according to the methods of the invention.

As will be clear to those skilled in the art, the invention enables the production in vitro of high volumes of T cells at various stages of development. It also enables in vitro test systems for analyzing the effect of an agent on T cell growth and development. It further enables a system for the production of genetically altered T cells which can be used inter alia in in vivo applications. The following general non-limiting examples will illustrate various uses of the invention; other uses will be immediately apparent to those skilled in the art.

The invention facilitates the study of T cell differentiation and growth by providing for the sequential development of high numbers of T cells into various stages of T cell development. Genes that are turned on and off can be identified and cloned via, for example, subtractive hybridization. The repertoire of receptors expressed at various stages also can be elucidated. The role of the thymus on T cell differentiation can be further elucidated. Greater quantities of molecules that are characteristic of particular stages of T cell development are available according to the invention. In general, intra and inter cellular events of T cell differentiation can be studied utilizing the invention.

The invention also facilitates the study of exogenously induced genetic changes to T cells and progenitors, including changes that result from infection by pathogens, such as those resulting in infectious disease and those associated with cancer, and changes that result in gene transfer for gene therapy purposes. For example, the cells and events associated with HIV infection can be studied more easily in vitro. Likewise, drug agents including gene therapy drug agents can be evaluated in vitro for their: protective effect against HIV infection or progression to disease. In general, laboratory evaluation of genetic therapies for disease of T cells can be studied in vitro. Such disease include, adenosine deaminase deficiency, purine nucleoside phosphorylase deficiency, leukocyte adhesion deficiency, and other congenital immune deficiency disorders involving T lymphocytes.

Ex vivo production of genetically altered T lymphocytes for introduction into a patient also is provided by the invention. Although hematopoietic stem cell therapy is generally conceived as involving reintroduction of genetically modified stem cells back into a patient, there can be advantages to differentiating genetically modified progenitor cells into T lymphocytes in vitro prior to reinfusion. These advantages include avoiding potential adverse affects of therapeutic genes in hematopoietic cells other than T cells, avoiding the many toxicities associated with bone marrow transplantation, and using stem cells as a source of genetically modified T cells for patients in whom CD4 T cell counts are not sufficient to support ex vivo expansion in reinfusion. Appropriate "education" of these in vitro derived T cells to recognize foreign antigens in the context of self major histocompatibility molecules and to avoid recognition of self (auto immunity) could be provided by the coculture of donor cells (e.g. fibroblasts or macrophages) with the rhesus thymic stroma culture. These cells could then be expanded by restimulation with feeder cells and reinfused. As an alternative technique, genetically modified cells could be removed from the monolayer at an immature stage prior to "education" (e.g. at the CD3+CD4+CD8+ stage) and reinfused into a patient where they would complete T cell maturation in vivo.

In general, the invention provides a method for expanding and differentiating cells in vitro, which cells then can be used for immune supplementation, necessary, for example, as a result of a genetic immune deficiency, aggressive treatment such as chemotherapy or radiation therapy and the like. In this regard, a subject's own cells can be removed, expanded and/or differentiated to a particular stage, as desired, and optionally genetically altered as discussed above. The cells then can be reintroduced into the subject at an appropriate time.

The invention also provides facilitated laboratory evaluation of drugs and cytokines that affect growth or differentiation of T cells, including those designed to enhance T cell production. Development of biologic agents to enhance production of specific hematopoietic cell lineages have been dependent on effective in vitro assays. Present assays are not suitable for testing large numbers of compounds for activity in enhancing the lymphopoiesis. However, given the reproducibility of the nonhuman primate thymic stroma culture system and the availability of large quantities of tissue, this system would be ideally suited for such large scale screening. Although it is possible that there may be some differences in the effects of the agents on, for example, human and rhesus tissue, because of the phylogenetic similarity of these species and the fact that multiple human cytokines are known to be active in rhesus tissue, it is likely that these interspecies differences will be minimal.

The invention may also facilitate in vitro transduction of hematopoietic stem cell or T progenitor cells. Transduction of cells using viral vectors generally requires cell division, and determination of the appropriate conditions for cell division in vitro remains a significant challenge for the development of gene therapy. Stimulation of cell division with cytokines can lead to terminal differentiation of cells and loss of pluripotency. Transduction of cells cultured on rhesus thymic stroma is likely to mimic natural stimuli for cell division and may allow more optimal introduction of foreign genes into lymphocyte progenitors.

As mentioned above, the invention also provides kits. The kits include a cryopreserved suspension of non-human primate thymic stromal cells together with instructions for coculturing such cells with primate hematopoietic T cell progenitor cells, preferably human cells.

EXAMPLES

Materials and Methods

Animals

Rhesus monkeys (*Macaca mulatta*) used in this study were normal, colony born animals maintained in accordance with the guidelines of the Committee on Animals of the Harvard Medical School and the Guide for the Care and Use of Laboratory Animals (DHHS Publication N. [NIH]85-23, revised 1985). For bone marrow aspirates animals were anesthetized with ketamine HCl and received lidocaine in situ.

Isolation of mononuclear cells from bone marrow and cord blood

Bone marrow was extracted from mature rhesus macaques using an Illinois sternal/iliac aspiration needle (Stuart, USA) and a heparinized syringe. One to three samples with volumes of 1 to 8 ml were aspirated per iliac crest.

Heparinized bone marrow was obtained from normal human volunteers who provided written informed consent to a New England Deaconess Hospital Institution Reviewed Boards approved protocol.

Five milliliters of venous cord blood was extracted using a heparinized syringe prior to the severing of the umbilical cord during a Caeserean section delivery of a Rhesus macaque. After the umbilical cord was severed and the infant extracted, the placenta was removed by clamping the umbilical vein proximally and severing distally to the placenta. Immediately after the placenta was removed the umbilical vein was unclamped and the blood contained in the placenta drained into an appropriate heparinized container. Before processing, the cord and placenta blood was mixed together.

After extraction the bone marrow or cord/placenta blood was diluted 2:1 with washing media (RPMI 1640, 10 IU/ml penicillin, 10 µg/ml streptomycin, 1 mM L-glutamine). The sample(s) were then underlayed with a volume of Ficoll-Hypaque (1.077 g/ml) equal to half of the diluted sample volume so that a distinct sample/Ficoll interface formed. After centrifugation for 45 minutes at 400×g the interface containing mononuclear cells was removed. The cells were then washed by resuspending in culture medium and centrifuging for 10 minutes at 400×g. The resulting pellet was resuspended in 6 ml of ammonium chloride lysing buffer (0.15M $NH_4Cl$, 1.0 mM $KHCO_3$, 0.1M $Na_2EDTA$) for 3 minutes to lyse any remaining erythrocytes. The suspension was then diluted with media and washed twice more. After the final wash the cells were resuspended in 1–2 ml media and the number of viable cells was determined by trypan blue exclusion.

Isolation of CD34 positive cells

Cells expressing the surface antigen CD34 were isolated using the Dynal CD34 Progenitor Cell Selection System (Dynal, Lake Success, N.Y.). The mononuclear cells isolated from bone marrow or umbilical cord blood were suspended in isolation buffer (PBS, 2% heat inactivated fetal bovine serum, 10 IU/ml penicillin, 10 µg/ml streptomycin) at a concentration of $2.5 \times 10^7$ cells/ml. The suspension was then added to magnetic anti-human CD34 beads that crossreact with rhesus CD34 (Dynal M-450 CD34) in a ratio of $4.0 \times 10^7$ beads per ml of suspension, in a round bottom tube. (Dynabeads M-450 CD34 are superparamagnetic beads bound to monoclonal antibody specific for CD34.) The mixture was vortexed gently and incubated at 4° C. for 45 minutes with gentle tilt rotation using a Dynal Sample Mixer. After incubation the bead/cell mixture was resuspended in a larger volume of isolation buffer and placed in a magnetic separation device for 2 minutes to allow the cell/bead complexes to accumulate to the tube wall. While still exposed to the agent, the suspension containing the cells not bound to the magnetic beads was aspirated. The cell/bead complexes were washed three more times in this manner, pooling the suspensions containing the CD34 negative cells into the same tube. The tube containing the released cells (CD34⁻) was then placed on the magnetic separator to remove any remaining beads and this supernatant was transferred to a new conical tube. All CD34+ cells attached to beads were washed twice in a minimum of 10 ml of isolation buffer with centrifugation at 2000 rpm for 8 min. Cells bound to magnetic beads were then resuspended in 100 ul of isolation buffer per $4 \times 10^7$ beads used, with a minimum volume of 100 µl. The CD34 positive cells were then detached from the beads by adding an equal volume of an anti-idiotype antibody (DETACHaBEAD CD34, Dynal), vortexing, and gently mixing at room temperature using a Dynal Sample Mixer for one hour. The cells were isolated from the cell/bead suspension by adding isolation buffer and placing the tube in the magnetic separation device for 2 minutes. After the beads migrated to the tube wall, the supernatant containing the CD34 positive cells was transferred to a new tube. The beads were washed three more times with the suspensions containing the released cells pooled into the same tube. The tube containing the released CD34⁺ cells was then placed on the magnetic separator to remove any remaining beads, and the supernatant was transferred to a new conical tube. The cells were washed twice in a minimum of 10 ml of isolation buffer with centrifugation at 2000 rpm for 10 minutes.

Blast forming unit/Colony forming unit (BFU/CFU) assays

After isolation, the bone marrow or cord/placenta mononuclear cells were diluted to a concentration 10-fold greater than the final desired plating concentration in plating media (DMEM with 2% heat inactivated fetal bovine serum). The final plating concentrations were: bone marrow, $1 \times 10^6$ cells/ml; cord/placenta blood, $1 \times 10^5$ cells/ml; and CD34 positive cell, $1 \times 10^4$ cells/ml. The following contents were then added to a 50 ml conical centrifuge tube for a total volume of about 3.15 ml: Iscove's DMEM with 10 IU/ml penicillin/10 µg/ml streptomycin/1 mM L-glutamine, rEPO (1 U/ml), rGM-CSF (1 ng/ml), rIL-3 (10–20 ng/ml), cell suspension (0.3 ml), and methyl cellulose (2.8 mi, Stem Cell Technologies, Vancouver, BC, Canada). The mixture was gently vortexed and allowed to stand for several minutes to remove air bubbles. The cell mixture was then added in duplicate to 35 mm cell culture dishes with grids with a syringe and blunt needle. After dispensing the mixture, any bubbles present were removed with the syringe. The duplicate plates were placed inside a 100 mm cell culture dish along with 3 ml sterile PBS to prevent desiccation. The plates were incubated in a 37° C. incubator with 5% $CO_2$. After two weeks the number of erythroid colonies and granulopoietic colonies were counted under a microscope. The erythroid colonies were distinguishable from the granulopoietic colonies based on the presence of a red hue caused by the hemoglobin contained in each cell. Appropriate conversions were made to the cell counts to account for the differences in staging dilutions.

Thymic monolayer cultures

Thymic tissue from third trimester (120–165 days, 165 days being full term) Rhesus fetuses delivered by Caesarean section was minced into small fragments (1 mm³) using blunt nosed scissors. The fragments were then digested into a single cell suspension by incubation in PBS with 0.5 mg/ml of collagenase (Sigma-C9407) and 2 units/ml DNase1 (Sigma-DN-25) at 37° C. for 60 minutes with frequent agitation. The solution was pipetted vigorously to break up any incompletely digested fragments. The number of viable cells was counted using a hemacytometer based on trypan blue exclusion by the viable cells. The cell suspension was washed once in culture media (RPMI 1640, 10% heat inactivated fetal bovine serum, 10 IU/ml penicillin, 10 µg/ml streptomycin, 1 mM L-glutamine) followed by centrifugation at 2000 rpm for 10 minutes. Cryopreservation of the thymic stromal cells was performed using a freezing solution of 90% fetal bovine serum and 10% dimethylsulfoxide. Thymic stromal cells used after cryopreservation and thawing fully supported the growth and differentiation of CD34⁺ cells. The suspension was placed into 24 well cell culture plates at a concentration of $5 \times 10^5$ to $1 \times 10^6$ cells per well in a volume of 2 ml culture medium. After two days in a 37° C. incubator with 5% $CO_2$, the nonadherent cells were removed and the adherent cell layer was washed three times with culture media to remove any loose cells. The monolayer was then maintained in culture media which was changed at least twice per week. After 6 days in culture, CD34 positive cells were added to the monolayer at concentrations ranging from $10^3$ to $10^5$ cells per well. After 14 days, cells were stimulated on the monolayer, using either 5 µg/ml Con A (concanavalin A, Sigma) or anti-rhesus CD3 (30 ng/ml) (6G12, provided by Dr. Johnson Wong; other anti-rhesus CD3 antibodies are commercially available or may be prepared by one of ordinary skill in the art) and anti-CD28 (30 ng/ml; Immunotech, Westbrook, Me.) in combination with $1 \times 10^6$ irradiated (3000 Rads) human peripheral blood mononuclear cells (PBMC) and 100 U/ml recombinant human IL-2 (Dr. Maurice Gately, Hoffman-LaRoche; may also be obtained from commercial sources). Cells may optionally be removed from the monolayer after 7 days and stimulated for expansion as described above.

Cells

Bone marrow stroma cultures were established in 24 well plates as described by Sutherland and Eaves (*Culture of Hematopoietic Cells*, pp. 136–162, 1994). Skin derived fibroblasts were obtained from skin biopsy samples that were minced into 1–2 mm pieces. These pieces were placed in a scored cell culture dish, covered with a sterile microscope slide, and incubated with growth medium containing DMEM with 20% FCS, 10 mM Hepes, 10 IU/ml penicillin, 10 mg/ml streptomycin, 10 µg/ml vancomycin and 10 µg/ml gentamycin. A confluent layer of fibroblasts was obtained after 10–14 days. Cells were removed from the plate by incubating in trypsin (0.05%)/EDTA (0.53 mM) for 2 minutes at 37° C. Cells were washed and replated in 24 well tissue culture plates at a concentration of $6 \times 10^4$ cells/well. Confluent cell layers were obtained in 3–4 days and bone marrow derived CD34⁺ cells were added to these wells.

Fluorescent antibody analysis

The distribution of CD3, CD4 and CD8 and other proteins on the differentiated CD34 positive cells removed from thymic monolayers was determined at varying stages of cell maturity by antibody binding and FAGS analysis. Antibodies used for immunophenotyping rhesus and human cells included anti-CD3 (6G12, rhesus specific; Kawai et al. Transplant Proc., 26:1845–1846, 1994), anti-CD4 (OKT4) (Ortho Diagnostics, Raritan, N.J.), anti-CD8 (Leu-2a) (Becton-Dickinson, San Jose, Calif.), anti-CD16 (Leu-11A) (Becton-Dickinson, San Jose, Calif.), anti-CD28 (Immunotech, Westbrook, Me.) and anti-CD34 (QBend-10) (Immunotech, Westbrook, Me.). An antibody specific for human CD3 (Leu-4) (Becton-Dickinson) was used in the xenogeneic studies. All antibodies used in the experiments were specific for human markers and cross-react with rhesus markers except the anti-CD3 (6G12) antibody which is specific for rhesus CD3. The presence of CD4 was detected by staining with anti-CD4 antibody (OKT4) directly conjugated to phycoerythrin (PE) (Ortho Diagnostics, Raritan, N.J.). The presence of CD3 was detected by staining with anti-CD3 antibody directly conjugated to FITC using the Quick Tag FITC Conjugation Kit (Boehringer Mannheim, Indianapolis, Ind.). The presence of CD8 was detected by staining with biotinylated anti-CD8 (Leu-2a) antibody (Becton-Dickinson, San Jose, Calif.). Streptavidin conjugated to the fluorescent dye Red 670 (GIBCO-BRL, Frederick, Md.) was used as a detection reagent for biotinylated anti-CD8 antibody. Cells were stained in the presence of staining media (PBS with 2% heat inactivated fetal bovine serum). After antibody staining the cells were either analyzed while viable in staining media or fixed with freshly prepared 2% paraformaldehyde. Three color flow cytometry analysis of the thymocytes was performed using a FACScan flow cytometer (Becton Dickinson).

Limiting dilution assay

Thymic monolayer cultures were established in 96 well plates as described above using $5 \times 10^4$ thymic stroma cells per well. Purified $CD34^+$ bone marrow derived cells were added to the 96 well plate in serial dilutions from 1000 to 1 cell per well in 24 well replicates for each serial dilution. Cultures were maintained as described above. Cell growth was evaluated after 14 days of culture by counting viable cells, using the criterion of a doubling of input cell number to establish growth. Growth of T cells in wells scored as positive based on cell numbers was confirmed by FACS analysis of cells; all wells analyzed (>10) confirmed growth of T lymphocytes in positive wells. Data was generated on a complimentary log—log plot assuming the number of positive wells follows a binomial distribution, and that the number of cells in any well follows a Poisson distribution. In wells with more than 1000 cells, immunophenotyping for CD3, CD4 and CD8 was performed as described above.

PKH26 labeling of CD34 cells

Purified $CD34^+$ cells ($1 \times 10^6$ cells) were transferred to a 15 ml polypropylene conical tube and washed once in medium without serum at 25° C. After centrifugation, cells were resuspended in 25° C. of serum free medium and rapidly mixed with PKH26 ($4 \times 10^6$ µm; Sigma) for 5 minutes at room temperature. The labeling reaction was stopped by the addition of 10% fetal bovine serum. Cells were washed three times and analyzed by fluorescence microscopy (546 nm excitation, Texas red filter cube) and flow cytometry (FACScan, Becton Dickinson) for efficiency of labeling. Labeled $CD34^+$ cells were added to monolayer cultures as described above.

mRNA extraction and cDNA synthesis

Messenger RNA was extracted from cells grown on a thymic monolayer harvested on a weekly basis over a four week period (Days 0, 7, 14, 21, 28). The extraction was performed using guanidinium thiocyanate and oligo dT spun columns (QuickPrep Micro mRNA Purification Kit; Pharmacia, Piscataway, N.J.) according to the manufacturer's instructions. mRNA samples were stored at −70° C. The first strand cDNA was synthesized in a 40 µl final volume, using approximately 2 µg of mRNA, 1 µg of random primer, and 6.25 units of AMV reverse transcriptase (GIBCO/BRL). Samples were incubated for 10 minutes at room temperature, 1 hour at 42° C., 5 minutes at 95° C., and 5 minutes at 4° C.

RT-PCR for RAG-2 gene expression cDNA was prepared by reverse transcription using random primers and Moloney MuLV reverse transcriptase (GIBCO-BRL, Grand Island, N.Y.). cDNA was amplified using primers specific for a 415 bp region of the human RAG-2 gene, which is expressed transiently only by cells undergoing lymphocyte differentiation. The oligonucleotide primers were synthesized on a model 394 DNA/RNA synthesizer (Applied Biosystems, Foster City, Calif.). The sequences of the RAG-2 primers were as follows: 5' primer: GTC CCG GGC GCT GCA (669–683; SEQ. I.D. NO. 1), 3' primer: CCT CCC ACA CGC TTG CAG T (1082–1064; SEQ. I.D. NO. 2) and probe: CGT TGG GTC GGT GTC AGC CAC TCT CAC CTC CC (701–733; SEQ. I.D. NO. 3). One quarter of the cDNA product was added to each PCR reaction (final volume 50 µl) with 50 pmole of each oligonucleotide primer and 2.5 U Taq DNA Polymerase (Pharmacia). PCR amplification was performed in a Gene-Amp 9600 thermal cycler (Perkin Elmer, Norwalk, Conn.) for 35 cycles of denaturation at 94° C. for 30 s, annealing at 60° C. for 30 s and extension at 72° C. for 30 s. PCR products were separated on 2% agarose gels containing ethidium bromide and photographed under UV light. Specificity was confirmed by Southern blot hybridization with a $^{32}$P-labelled 32-nucleotide RAG-2 probe. 13-actin primers (Clontech, Palo Alto, Calif.) were used to amplify the cDNA as a control.

RT-PCR analysis of TCR Vβ gene expression

Expression of the 25 Vβ gene subtypes was determined by RT-PCR. A PCR reaction mixture (45 µl) containing 1.5 mM $MgCl_2$, 0.100 mM of each dNTP, 2.5 units of Taq polymerase, and 27.0 pmol of the antisense C13 primer was aliquoted from a master mix into 0.2 ml Microamp tubes (Perkin Elmer) each containing 27.0 pmol of each Vβ primer (Vβ1-24) (Chen et al., J. Immunol., 151:2177–2187, 1993). cDNA from each time point (5 µl) was aliquoted into each 45 µl reaction tube. In addition two controls were run simultaneously in separate reaction tubes for each time point: Cβ primers as an internal control, and β-Actin to confirm the integrity of the cDNA. A water control containing no cDNA was also run with each set of reactions to rule out contamination. PCR amplification was performed in a Gene Amp 9600 thermal cycler. Reaction conditions were a modified hot start followed by 30 cycles of 94° C., 55° C. and, 72° C. for 1 minute each. PCR products were run on a 1.5% agarose gel containing ethiduim bromide and photographed under UV light.

Example 1

Immunophenotyping of Rhesus Bone Marrow

The surface phenotype of freshly isolated rhesus bone marrow was determined by staining with fluorescent antibodies and subsequent FACS analysis. Approximately 30% of all bone marrow mononuclear cells expressed CD34 and the level of CD34 expression varied markedly in this population from $CD34^{lo}$ to $CD34^{hi}$, with the majority of cells expressing low to intermediate levels of CD34. Approximately 1–4% of the $CD34^+$ cells express high levels of this epitope, and these are presumed to be enriched for the uncommitted or pluripotent hematopoietic progenitor cells. Cells isolated by immunomagnetic separation were 95% pure for CD34 expression as determined by flow cytometry, and were greatly enriched for the population of progenitors expressing high surface levels of CD34.

Analysis of purified $CD34^+$ cells did not reveal any cells with the phenotype of mature or immature T lymphocytes. A small percentage of $CD34^+$ cells were shown to express CD4. A variable percentage of $CD34^{lo}$ cells expressed high levels of CD2, but these cells were negative for CD3 expression. A small discrete population of $CD34^+$ cells were found to coexpress CD8. However, neither the $CD2^+$, $CD4^+$ or $CD8^+$ subpopulations were shown to coexpress CD3, indicating the absence of a T cell receptor complex and demonstrating the absence of a significant number of contaminating T cells.

Example 2

Immunohistochemistry of Thymic Stromal Cells

Immunohistochemistry was performed on thymic monolayers, and determined that a heterogeneous population of cells was present. Positive staining was detected with: antibodies directed against desmin and vimentin, indicating myofibroblasts; antibodies directed against cytokeratins, indicating epithelial cells; and antibodies against CD68 and CD14 indicating macrophages. In addition expression of both MHC class I and MHC class II was detected. The structure of the adherent cell layer was described as non-uniform with discrete raised areas that exhibit the greatest staining for antibodies directed against macrophage epitopes, epithelial cells and MHC class II. The thymic cells thus appear to develop some form of three dimensional structure in culture.

Example 3

Differentiation of $CD3^+$ T Lymphocytes from $CD34^+$ Cells on Rhesus Thymic Monolayers In order to assess the ability of an in vitro system to support T lymphocyte differentiation, purified rhesus bone marrow or cord blood derived $CD34^+$ cells were cultured on rhesus thymic stroma monolayers. Wells inoculated with $5 \times 10^4 - 1 \times 10^5$ purified $CD34^+$ cells showed an average expansion in cells to $7.2 \times 10^5$ by day 14. On day 14 of culture, flow cytometric analysis revealed the presence of a discrete population of cells with a forward and side scatter profile characteristic of lymphocytes. By three color flow cytometry, these cells were found to consist of $CD3^+CD4^+CD8^+$ (double positive) cells characteristic of immature T lymphocytes and $CD3^+CD4^+CD8^-$ and $CD3^+CD4^-CD8^+$ single positive T lymphocytes. After 21 days in culture, 96% of gated cells were CD3 positive and coexpressed either CD4 or CD8. Similar results were obtained with bone marrow or cord blood $CD34^+$ derived cells. Compared with day 14, these cells exhibited a more mature phenotype, with a decrease in the number of double positive cells, and an increase in the numbers of $CD3^+CD4^+CD8^-$ and $CD3^+CD4^-CD8^+$ single positive thymocytes. Stimulation with either anti CD3 and anti CD28 antibodies or ConA in the presence of irradiated human peripheral blood mononuclear cells (PBMC) generated as many as $3 \times 10^7$ $CD3^+$ single positive cells. A subpopulation of cells was observed that exhibited a higher forward and side scatter profile. FACS analysis demonstrated these cells to express the phenotype $CD3^+CD4^-CD8^{lo}CD16^+$. The surface level of CD3 in this population varied from low to intermediate. This phenotype is characteristic of natural killer cells.

Example 4

$CD3^+$ Lymphocytes are Derived from $CD34^+$ Cells

A number of studies were conducted to demonstrate that the T lymphocytes observed in culture were derived from the $CD34^+$ cells and dependent on thymic tissue. Control experiments included culture of: 1) CD34-depleted bone marrow on rhesus thymic stroma; 2) $CD34^+$ purified cells on bone marrow stroma; and 3) $CD34^+$ cells cultured on rhesus fibroblasts.

These conditions were universally negative for generating the appropriate milieu for $CD34^+$ cells to develop into T lymphocytes. These experiments demonstrated that the effects observed in culture were specific to the thymic monolayers, and dependent on $CD34^+$ cells. The only conditions that resulted in the development of both double and single positive thymocytes and natural killer cells was the addition of $CD34^+$ bone marrow derived cells to thymic monolayer cultures. This demonstrates that lymphoid progenitors are present in $CD34^+$ purified fractions of bone marrow.

Further evidence to demonstrate that the $CD3^+$ lymphocytes developed from $CD34^+$ bone marrow derived cells was provided by assays using PKH26 labeling of $CD34^+$ cells. We achieved close to 100% labeling of $CD34^+$ cells at the time of labeling, as determined by flow cytometry. The presence of PKH26 was observed in both double positive and single positive $CD3^+$ lymphocytes derived from PKH26 labeled $CD34^+$ cells grown on thymic monolayers. The level of cell membrane labeling with PKH26 was observed to decrease with the cells' maturity and time in culture. This was expected as PKH26 is incorporated stably into the membrane of the primary labeled cells; thus the mount of PKH26 per cell will decrease exponentially with each cell division. PKH26 labeled cells were shown to express CD3, CD4 and CD8 on their cell surface, demonstrating that the $CD34^+$ bone marrow derived cells had developed into T lymphocytes.

Example 5

Estimation of Lymphoid Precursor Frequency by Limiting Dilution Assay

A single stem cell has the ability to generate multiple progeny via the process of differentiation. We determined the precursor frequency of purified $CD34^+$ cells by quantification of the number of viable thymocytes and T cells that could be generated in thymic monolayer cultures. Data from representative limiting dilution assays determined the precursor frequency to be $1/93$ ($1/68-1/128$), with a chi square of 12.3, for lymphocyte progenitors from $CD34^+$ bone marrow.

Example 6

Differentiation of Human $CD34^+$ Cells into T Cells on Rhesus Monolayers

Parallel experiments examined the characteristics of the thymic monolayers in a xenogeneic system. Human bone marrow derived $CD34^+$ cells grown under the same conditions on rhesus thymic monolayers generated $CD3^+CD4^+CD8^+$, $CD3^+CD4^+CD8^-$ and $CD3^+CD4^-CD8^+$ cells. Flow cytometry analysis was performed with an anti-CD3 antibody that is specific for human CD3, which provides further data to demonstrate that the exogenously added $CD34^+$ cells develop into T cells in a thymic monolayer environment. A rhesus specific CD3 antibody failed to bind to the T cell progeny isolated from the monolayers, confirming the absence of rhesus T cells. The level of CD3 staining demonstrated tripartite distribution characteristic of thymocytes.

Example 7

$CD3^+$ T Lymphocytes Derived from Thymic Monolayers Are Functional

Cells derived from thymic monolayers were shown to be responsive to a number of proliferation signals characteristic of thymocytes and T cells. Our results show that from 14 days in culture, there is a population of cells present that respond to stimulation with lectin in the presence of irradiated feeders, and this results in expansion of the cell numbers. Our data demonstrate that this method of stimulation employed every 14 days resulted in marked expansion of T cell progeny in culture, as shown in Table 1. The cells exhibited characteristics unique to thymocytes when stimulated with anti-CD3 antibody alone. In this situation, cell numbers decreased, demonstrating a poor response to anti-CD3. However, when anti-CD28 was provided as a costimulation, we observed significant expansion of the T cell population, with expansion of both double and single positive thymocytes. Anti-CD28 alone failed to yield a proliferative response.

TABLE 1

Response of T cells from thymic monolayer cultures to mitogenic stimuli.

| Expt. | Day 0 | Day 14 | Stimulus | Day 28 | Day 42 | Day 56 | Day 70 |
|---|---|---|---|---|---|---|---|
| 1 | $0.1 \times 10^6$ | $0.05 \times 10^6$ | lectin | $2 \times 10^6$ | $10 \times 10^6$ | $16 \times 10^6$ | $225 \times 10^6$ |
| 2 | $0.1 \times 10^6$ | $0.2 \times 10^6$ | lectin | $2.1 \times 10^6$ | $4 \times 10^6$ | $64 \times 10^6$ | $60 \times 10.6$ |
| 3 | $0.08 \times 10^6$ | $0.2 \times 10^6$ | lectin | $4.5 \times 10^6$ | $18 \times 10^6$ | $16 \times 10^6$ | $27 \times 10^6$ |
| 4 | $0.1 \times 10^6$ | $1.5 \times 10^6$ | antiCD3/CD28 | $3.2 \times 10^6$ | $9 \times 10^6$ | $99 \times 10^6$ | $17 \times 10^6$ |
| 5 | $0.1 \times 10^6$ | $1.6 \times 10^6$ | antiCD3 | $0.08 \times 10^6$ | $0.04 \times 10^6$ | — | — |
| 6 | $0.1 \times 10^6$ | $0.8 \times 10^6$ | antiCD28 | $0.05 \times 10^6$ | — | — | — |

Representative cell counts of samples generated from thymic monlayer cultures. Cell number is the total viable cell number as determined by trypan blue exclusion. Cells from experiments 1, 2 and 3 were stimulated with Con A every 14 days. Experiment 4 was stimulated with anti CD3 and anti CD28 antibodies at day 14 and then with Con A every 14 days. Experiment 5 was stimulated with anti CD3 alone at day 14, and then Con A at day 28. Cells were stimulated with indicated mitogens in the presence of irradiated human PBMC and 100 U/ml rIL-2. Numbers of cells selected time points reflect calculated total cell number based on the observed expansion of a subset of total cells.

The cultures remained responsive to either lectin or anti-CD3 and anti-CD28 restimulation for 6–12 weeks. Cultures could thus be maintained for protracted periods, and allowed the generation of large numbers of T cells from $CD34^+$ bone marrow derived cells.

Example 8

Temporal Expression of Lymphoid Lineage Genes

Commitment to lymphopoiesis is accompanied by a highly regulated process of differentiation, which is characterized by the temporal expression of various lymphoid lineage associated genes. Expression of the T lymphocyte associated gene products, namely TCR and RAG-2, were determined at sequential time points by RT-PCR. The $CD34^+$ purified population was devoid of both TCR and RAG-2 gene products. At day 7 and 14 cells derived from the thymic monolayers were observed to express products of the RAG-2 gene. Expression of RAG gene products is required for rearrangement of the antigen receptor. Subsequent to day 14 the level of RAG-2 expression decreased. Simultaneous analysis of TCR gene products by RT-PCR detection demonstrated that TCR products were present subsequent to RAG-2 expression. TCR gene products were detected from day 14 onwards in cells derived from thymic monolayer cultures.

Example 9

Analysis of TCR Vβ Subsets

To further analyze the diversity of T cells that developed in this in vitro system, RT-PCR determination of TCR Vβ subsets was performed at weekly intervals. Results were uniformly negative at both day zero ($CD34^+$ purified cells) and at day seven. Our results demonstrate that by day 14, 23 out of 25 Vβ subsets were detectable by RT-PCR. At day 14 the cultures underwent stimulation with lectin and IL-2. Subsequent analysis of the RNA present at day 28 indicated the presence of 21 out of 25 TCR Vβ subsets, suggesting that the lectin stimulation may result in selective expansion of certain Vβ subsets.

Those skilled in the art will be able to ascertain with no more than routine experimentation numerous equivalents to the specific processes and products described herein. Such equivalents are considered to be within the scope of the invention and are intended to be embraced by the following claims:

---

We claim:

1. A method for in vitro T cell production, comprising:
coculturing in vitro a monolayer of non-human primate thymic stromal cells with primate hematopoietic T cell progenitor cells.

2. The method of claim 1, wherein the hematopoietic T cell progenitor cells are derived from a member of the species *Homo sapiens*.

3. The method of claim 1, wherein the hematopoietic T cell progenitor cells are derived from a member of the species *Macaca mulatta*.

4. The method of claim 1, wherein the thymic stromal cells are derived from a member of the species *Macaca mulatta*.

5. The method of claim 2, wherein the thymic stromal cells are derived from a member of the species *Macaca mulatta*.

6. The method of claim 3, wherein the thymic stromal cells are derived from a member of the species *Macaca mulatta*.

7. The method of claim 1, further comprising:
isolating the hematopoietic T cell progenitor cells or descendants thereof from the monolayer of thymic stromal cells prior to the differentiation of hematopoietic T cell progenitor cells into predominantly $CD3^+4^+8^-$ and $CD3^+4^-8^+$ cells.

8. The method of claim 7, further comprising:
culturing the isolated cells with a mitogenic expansion agent to stimulate mitogenic expansion of the isolated cells or descendants thereof;
isolating the expanded population of cells; and
coculturing the expanded population of cells with a monolayer of thymic stromal cells.

9. The method of claim 7, wherein the predominant cell type isolated is $CD3^+4^+8^+$ cells.

10. The method of claim 1, further comprising:
isolating the hematopoietic T cell progenitor cells or descendants thereof from the monolayer of thymic stromal cells; and
culturing the isolated cells with a mitogenic agent to stimulate expansion of the isolated cells.

11. The method of claim 10, wherein the mitogenic agent is nonmitotic feeder cells.

12. The method of claim 1, further comprising:
coculturing in vitro the monolayer of thymic stromal cells and the hematopoietic T cell progenitor cells in the presence of an agent capable of genetically altering the hematopoietic T cell progenitor cells; and
isolating at least one genetically altered hematopoietic T cell progenitor cell or descendant thereof.

13. The method of claim 1, wherein the hematopoietic T cell progenitor cells are genetically altered T cell progenitor cells.

14. The method of claim 5, further comprising:

isolating the hematopoietic T cell progenitor cells from the monolayer of thymic stromal cells; and coculturing the isolated cells with irradiated peripheral blood lymphocytes in the presence of interleukin-2 to stimulate expansion of the isolated cells.

15. A method for testing the effect of an agent on cells, comprising:

coculturing in vitro a monolayer of non-human primate thymic stromal cells with primate hematopoietic T cell progenitor cells in the presence of the agent; and comparing differentiation or growth of the T cell progenitor cells, or descendants thereof, exposed to the agent to the differentiation or growth of control T cell progenitor cells or descendants thereof as a determination of the effect of the agent.

16. The method of claim 15, wherein the hematopoietic T cell progenitor cells are derived from a member of the species *Homo sapiens*.

17. The method of claim 15, wherein the hematopoietic T cell progenitor cells are derived from a member of the species *Macaca mulatta*.

18. The method of claim 15, wherein the thymic stromal cells are derived from the thymus of a member of the species *Macaca mulatta*.

19. The method of claim 18, wherein the hematopoietic T cell progenitor cells are derived from a member of the species *Homo sapiens*.

20. The method of claim 15, wherein the hematopoietic T cell progenitor cells are genetically altered T cell progenitor cells.

21. A kit comprising:

a container containing a cryopreserved non-human primate thymic stromal cell suspension; and instructions for coculture of the thymic stromal cells with primate hematopoietic T cell progenitor cells.

22. An article of manufacture comprising:

a container containing a representative population of T cells derived by the method of claim 1.

* * * * *

UNITED STATES PATENT AND TRADEMARK OFFICE
CERTIFICATE OF CORRECTION

| | |
|---|---|
| PATENT NO. | : 5,677,139 |
| APPLICATION NO. | : 08/426782 |
| DATED | : October 14, 1997 |
| INVENTOR(S) | : R. Paul Johnson et al. |

It is certified that error appears in the above-identified patent and that said Letters Patent is hereby corrected as shown below:

In the Specification

At Column 1, Lines 5-10, please change the sentence:
"This invention was supported by NIH Grant NOS.RROO168,AI36559 and HL44851, and the government has certain rights to the invention."

To:
-- This invention was made with government support under RR000168, HL044851, and AI036550 awarded by the National Institutes of Health. The government has certain rights in the invention. --

Signed and Sealed this
Sixth Day of August, 2024

*Katherine Kelly Vidal*
*Director of the United States Patent and Trademark Office*